United States Patent [19]

Lesher et al.

[11] 4,374,141
[45] Feb. 15, 1983

[54] 2-SUBSTITUTED AMINO-5-(PYRIDINYL)-NICOTINAMIDES AND THEIR CARDIOTONIC USE

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 293,248

[22] Filed: Aug. 17, 1981

[51] Int. Cl.³ .................. C07D 401/04; A61K 31/455
[52] U.S. Cl. ....................................... 424/266; 546/257
[58] Field of Search ............... 546/257, 258, 259, 260; 544/131; 424/263, 266, 248.54

[56] References Cited

U.S. PATENT DOCUMENTS

| | | |
|---|---|---|
| 4,107,315 | 8/1978 | Lesher et al. .................. 546/257 |
| 4,264,603 | 4/1981 | Lesher et al. . |
| 4,264,612 | 4/1981 | Lesher et al. . |
| 4,297,360 | 10/1981 | Lesher et al. .................. 546/257 |

OTHER PUBLICATIONS

Baldwin et al., J. Med. Chem. 20, 1189–1193, (1977).

*Primary Examiner*—John M. Ford
*Attorney, Agent, or Firm*—Robert K. Bair; B. Woodrow Wyatt; Paul E. Dupont

[57] ABSTRACT

Shown is a process for preparing cardiotonically active 1,3-dihydro-3-R-6-PY-5-Q-2H-imidazo[4,5-b]pyridin-2-ones, where Q is hydrogen or lower-alkyl, R is lower-alkyl, lower-hydroxyalkyl, lower-alkoxyalkyl or Y-NB where Y is lower-alkylene and NB is di-(lower-alkyl)amino or 4-morpholinyl, and PY is 4- or 3-pyridinyl or 4- or 3-pyridinyl having one or two substituents, by reacting a 2-RNH-5-PY-6-Q-nicotinamide with an alkali metal hypohalite. Also shown are cardiotonic compositions and a method for increasing cardiac contractility using 2-RR'N-5-PY-6-Q-nicotinamides or pharmaceutically acceptable acid-addition salts thereof, where R' is hydrogen or methyl. Also shown is the process for preparing said 2-RR'N-5-PY-6-Q-nicotinamides by reacting a 2-halo-5-PY-6-Q-nicotinamide with an amine of the formula RR'NH.

11 Claims, No Drawings

2-SUBSTITUTED AMINO-5-(PYRIDINYL)-NICOTINAMIDES AND THEIR CARDIOTONIC USE

CROSS-REFERENCE TO RELATED APPLICATIONS

Copending applications Ser. Nos. 135,105, filed Mar. 28, 1980 and now U.S. Pat. No. 4,294,837, issued Oct. 13, 1981, and 236,147, filed Feb. 20, 1981 as a division of Ser. No. 135,105 and now U.S. Pat. No. 4,309,537, issued Jan. 5, 1982, show the preparation of cardiotonically active 1,3-dihydro-1(or 3)-substituted-6-(pyridinyl)-2H-imidazo[4,5-b]pyridin-2-ones by reacting a 5-(pyridinyl)pyridine-2,3-diamine derivative with urea or carbonyldiimidazole.

BACKGROUND OF THE INVENTION (a) Field of the Invention

This invention relates to a process for preparing cardiotonically active 3-substituted-2H-imidazo[4,5-b]pyridin-2-ones, to intermediate 2-substituted-amino-5-(pyridinyl)nicotinamides therefor and to the preparation and cardiotonic use of said intermediates.

(b) Description of the Prior Art

Lesher and Gruett U.S. Pat. No. 4,264,603, issued Apr. 28, 1981, shows the reaction of a 2-halo-5-(pyridinyl)nicotinonitrile with a hydrazine to produce 5-(pyridinyl)-1H-pyrazolo[3,4-b]pyridin-3-amines, which are useful as cardiotonics.

Lesher and Gruett U.S. Pat. No. 4,264,612, issued Apr. 28, 1981, shows lower-alkyl 2-halo-5-(pyridinyl)-nicotinates and their use as intermediates for preparing 1,2-dihydro-5-(pyridinyl)-3H-pyrazolo[3,4-b]pyridin-3-ones and their use as cardiotonics, and also shows as intermediates 2-halo-5-(pyridinyl)nicotinoyl halides.

Baldwin et al [J. Med. Chem. 20, 1189–1193 (1977)] prepared 2-(3-pyridinyl)-1H-imidazo[4,5-b]pyridine and 2-(4-pyridinyl)-1H-imidazo[4,5-b]pyridine by heating respectively, a mixture of 2,3-diaminopyridine and nicotinic acid or a mixture of 2,3-diaminopyridine and isonicotinic acid. Both of these compounds were found by Baldwin et al to be inactive when tested as inhibitors of xanthine oxidase.

SUMMARY OF THE INVENTION

The invention in a process aspect comprises reacting a 2-RNH-5-PY-6-Q-nicotinamide with an alkali hypohalite to produce 1,3-dihydro-3-R-6-PY-5-Q-2H-imidazo]4,5-b]pyridin-2-one where R, PY and Q are defined hereinbelow.

The invention in another process aspect comprises reacting a 2-halo-5-PY-6-Q-nicotinamide with an amine of the formula RR'NH to produce 2-RR'N-5-PY-6-Q-nicotinamide where R, R', PY and Q are defined hereinbelow.

The invention in a composition of matter aspect resides in a 2-RR'N-5-PY-6-Q-nicotinamide where R, R', PY and Q are defined hereinbelow.

A composition aspect of the invention resides in a cardiotonic composition for increasing cardiac contractility comprising a pharmaceutically acceptable carrier and, as the active ingredient thereof, a cardiotonically effective amount of 2-RR'N-5-PY-6-Q-nicotinamide or pharmaceutically acceptable acid-addition salt thereof.

In a method aspect the invention resides in a method for increasing cardiac contractility in a patient requiring such treatment which comprises administering a medicament comprising a pharmaceutically acceptable carrier and, as the active component thereof, a cardiotonically effective amount of 2-RR'N-5-PY-6-Q-nicotinamide or pharmaceutically acceptable acid-addition salt thereof.

DETAILED DESCRIPTION INCLUSIVE OF PREFERRED EMBODIMENTS

The invention in a process aspect comprises reacting a 2-RNH-5-PY-6-Q-nicotinamide with an alkali hypohalite to produce 1,3-dihydro-3-R-6-PY-5-Q-2H-imidazo[4,5-b]pyridin-2-one having the formula I

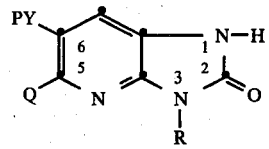

where Q is hydrogen or lower-alkyl, R is lower-alkyl, lower-hydroxyalkyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents. The compounds of formula I and their utility as cardiotonic agents are disclosed in said allowed copending Application Ser. No. 135,105, the disclosure of which is hereby incorporated by reference. Preferred embodiments of this process aspect are those where the alkali hypohalite is sodium hypochlorite and wherein PY is 4-pyridinyl or 3-pyridinyl, R is methyl, ethyl, 2-hydroxyethyl or 2-hydroxypropyl, and Q is hydrogen, methyl or ethyl, and especially where PY is 4-pyridinyl.

The compounds of formula I may exist in tautomeric forms, that is, as 1,3-dihydro-3-R-6-PY-5-Q-2H-imidazo[4,5-b]pyridin-2-ones of formula I and/or 3-R-6-PY-5-Q-3H-imidazo[4,5-b]pyridine-2-ols of formula IA, illustrated as follows

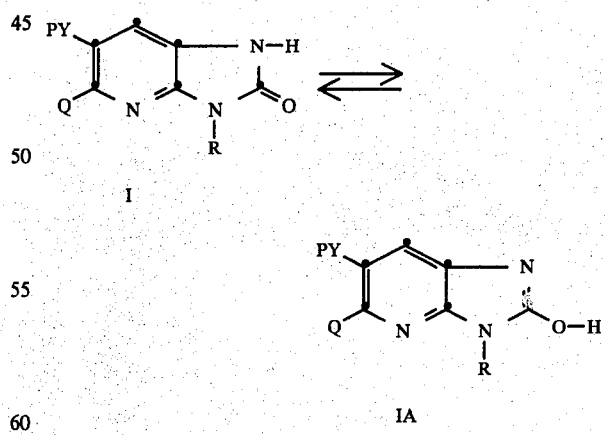

Structural preferences for other known imidazo[4,5-b]pyridin-2-ones would indicate the above formula I to be the preferred tautomeric structure; thus, we have preferred to use the names based on structure I, although it is understood that either or both structures (I or IA) are comprehended herein as the products produced by the process of the invention.

In another process aspect the invention comprises reacting 2-halo-5-PY-6-Q-nicotinamide with an amine of the formula RR'NH to produce 2-RR'N-5-PY-6-Q-nicotinamide where halo is chloro or bromo, R is lower-alkyl, lower-hydroxyalkyl, lower-alkoxyalkyl or Y-NB where Y is lower-alkylene having at least two carbon atoms between its connecting linkages and NB is di-(lower-alkyl)amino or 4-morpholino, R' is hydrogen or methyl, and PY is 4- or 3-pyridinyl or 4- or 3-pyridinyl having one or two lower-alkyl substituents. Preferred embodiments of this process aspect are those wherein PY is 4-pyridinyl or 3-pyridinyl, R is methyl, ethyl, 2-hydroxyethyl or 2-hydroxypropyl, R' is hydrogen or methyl, and Q is hydrogen, methyl or ethyl, and especially where PY is 4-pyridinyl.

In a composition of matter aspect the invention resides in 2-RR'N-5-PY-6-Q-nicotinamide having the formula II

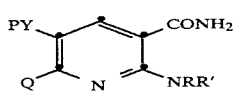   II where Q is hydrogen or lower-alkyl, R is lower-alkyl, lower-hydroxyalkyl, lower-alkoxyalkyl or Y-NB where Y is lower-alkylene having at least two carbon atoms between its connecting linkages and NB is di-(lower-alkyl)amino or 4-morpholino, R' is hydrogen or methyl, and PY is 4- or 3-pyridinyl or 4- or 3-pyridinyl having one or two lower-alkyl substituents, or pharmaceutically acceptable acid-addition salt thereof. The compounds of formula II are useful as cardiotonic agents, as determined by standard pharmacological evaluation procedures. Further, the compounds of formula II where R' is hydrogen are used as intermediates in said process aspect of the invention for preparing the compounds of formula I. Preferred embodiments of this aspect of the invention are the compounds where PY is 4-pyridinyl or 3-pyridinyl, R is methyl, ethyl, 2-hydroxyethyl or 2-hydroxypropyl, R' is hydrogen or methyl, and Q is hydrogen, methyl or ethyl. Particularly preferred embodiments are the compounds of formula II where R is methyl, ethyl, 2-hydroxyethyl or 2-hydroxypropyl, R' is hydrogen or methyl, PY is 4-pyridinyl and Q is hydrogen, methyl or ethyl.

A composition aspect of the invention resides in a cardiotonic composition for increasing cardiac contractility, said composition comprising a pharmaceutically acceptable carrier, and, as the active component thereof, a cardiotonically effective amount of 2-RR'N-5-PY-6-Q-nicotinamide of formula II, where Q, R, R' and PY are each defined as in formula II or pharmaceutically acceptable acid-addition salt thereof. Preferred embodiments are those having as active components the above said preferred embodiments of formula II.

A method aspect of the invention resides in the method for increasing cardiac contractility in a patient requiring such treatment which comprises administering orally or parenterally in a solid or liquid dosage form to such patient said cardiotonic composition comprising a pharmaceutically acceptable carrier and, as the active component thereof, a cardiotonically effective amount of a 2-RR'N-5-PY-6-Q-nicotinamide of formula II where Q, R, R' and PY are each defined as in formula II or a pharmaceutically acceptable acid-addition salt thereof.

The term "lower-alkyl" as used herein, e.g., as one of the meanings for R or Q or as a substituent for PY in formula I or II, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-pentyl, n-hexyl, and the like.

Illustrative of PY in formula I or II where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., as one of the meanings for R in formula I or II, means hydroxyalkyl radicals having from two to six carbon atoms which can be arranged as straight or branched chains and having at least two carbon atoms between hydroxy and the nitrogen atom of the imidazo[4,5-b]pyridine ring, illustrated by 2-hydroxyethyl, 3-hydroxypropyl, 2-hydroxypropyl, 4-hydroxybutyl, 3-hydroxybutyl, 5-hydroxypentyl, 6-hydroxyhexyl, and the like.

The term "lower-alkoxyalkyl" as used herein, e.g., as one of the meanings for R in formula I or II, means alkoxyalkyl radicals having from three to six carbon atoms which can be arranged as straight or branched chains and having at least two carbon atoms between the oxygen atom of alkoxyalkyl and the nitrogen atom of the imidazo[4,5-b]pyridine ring, illustrated by 2-methoxyethyl, 2-ethoxyethyl, 3-methoxypropyl, 2-methoxypropyl, 2-methoxybutyl, 4-ethoxybutyl, 3-ethoxypropyl, 3-n-propoxypropyl, and the like.

The term "lower-alkylene" used to define Y in the substituent Y-NB herein means lower-alkylene radicals having at least two carbon atoms between its connecting linkages and having from two to six carbon atoms which can be arranged as branched or straight chains, illustrated by

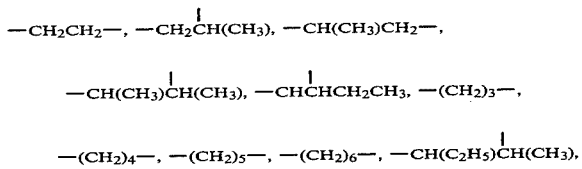

and the like.

The compounds of this invention having formula II are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base form, the hydrochloride or the methanesulfonate salt; however, appropriate pharmaceutically acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, ethanesulfonate, benzenesulfonate, cyclohexylsulfamate and quinate, respectively.

The acid-addition salts of said basic compounds (II) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds (II) are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of formula II were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same.

The intermediate 2-halo-5-PY-6-Q-nicotinamides used in a process aspect of the invention are prepared from known compounds, e.g., either by hydrolyzing a 2-halo-5-PY-6-Q-nicotinonitrile (U.S. Pat. No. 4,264,603) by heating it with concentrated sulfuric acid or by reacting a 2-halo-5-PY-6-Q-nicotinoyl halide (U.S. Pat. No. 4,264,612) with concentrated ammonium hydroxide.

The preparation of 2-RR'N-5-PY-6-Q-nicotinamides (II) is carried out by reacting a 2-halo-5-PY-6-Q-nicotinamide with RR'NH. The reaction is conveniently run by heating the reactants in a suitable solvent at about 75° C. to 150° C., preferably about 80° C. to 125° C., a preferred procedure being run in refluxing pyridine which acts not only as solvent but also as an acid-acceptor to take up the hydrogen halide produced by the reaction. Alternatively, the reaction can be run by autoclaving the reactants in the absence or preferably in the presence of a suitable solvent, preferably ethanol. Other suitable solvents include dimethylformamide and other lower-alkanols, e.g., isopropyl alcohol, n-propanol.

The reaction of a 2-RNH-5-PY-6-Q-nicotinamide (II) with an alkali metal hypohalite to produce 1,3-dihydro-3-R-6-PY-5-Q-imidazo[4,5-b]pyridin-2-one (I) is carried out by first mixing the reactants in an aqueous alkaline medium at about 20° C. to 30° C., next heating the reaction mixture at about 75° C. to 125° C., preferably about 90° C. to 110° C. and then making the reaction slightly acidic, preferably using acetic acid with cooling. The alkali hypohalite, preferably sodium hypochlorite, can be added directly or can be prepared in situ by reacting chlorine or bromine with aqueous alkali metal hydroxide.

The following examples will further illustrate the invention without, however, limiting it thereto.

A. 2-HALO-5-PY-6-Q-NICOTINAMIDES

A-1. 2-Chloro-5-(4-pyridinyl)nicotinamide [via 2-chloro-5-(4-pyridinyl)nicotinoyl chloride]—A mixture containing 216.2 g. of 2-oxo-5-(4-pyridinyl)nicotinic acid, two liters of phosphorous oxychloride and 4.0 ml. of dimethylformamide was heated with stirring on a steam bath for about 21 hours. Most of the phosphorous oxychloride was distilled off in vacuo and the remaining oily material was treated with chilled ammonium hydroxide with stirring. The precipitated product was collected and dried at about 80°–85° C. in a vacuum oven for 16 hours to yield 205.6 g. of 2-chloro-5-(4-pyridinyl)nicotinamide m.p. >310° C. This intermediate product was used without further purification in the reaction with the amine, RR'NH, to produce the 2-RR'N-5-(4-pyridinyl)nicotinamides of Example B.

A-2. 2-Chloro-5-(4-pyridinyl)nicotinamide [via 2-chloro-5-(4-pyridinyl)nicotinonitrile]—A mixture containing 150 g. of 2-chloro-5-(4-pyridinyl)nicotinonitrile and 1 liter of concentrated sulfuric acid was heated with stirring on a steam bath for 1 hour. The reaction mixture was cooled and poured into ice; and, the resulting mixture was made basic by adding concentrated ammonium hydroxide solution. The resulting product was collected, washed successively with water, ethanol and ether and then air-dried to yield 134 g. of 2-chloro-5-(4-pyridinyl)nicotinamide.

Following the procedure of Example A-1 or A-2 but using in place of 2-oxo-5-(4-pyridinyl)nicotinic acid or 2-chloro-5-(4-pyridinyl)nicotinonitrile a molar equivalent quantity of the appropriate 2-halo-5-PY-6-Q-nicotinic acid or 2-halo-5-PY-6-Q-nicotinonitrile, it is contemplated that the corresponding 2-halo-5-PY-6-Q-nicotinamides of Examples A-3 thru A-20 can be obtained.

A-3. 2-Chloro-5-(3-pyridinyl)nicotinamide.
A-4. 2-Chloro-5-(2-methyl-3-pyridinyl)nicotinamide.
A-5. 2-Chloro-5-(5-methyl-3-pyridinyl)nicotinamide.
A-6. 2-Chloro-5-(3-ethyl-4-pyridinyl)nicotinamide.
A-7. 2-Chloro-5-(2-methyl-4-pyridinyl)nicotinamide.
A-8. 2-Chloro-5-(2,6-dimethyl-4-pyridinyl)nicotinamide.
A-9. 2-Bromo-5-(4-pyridinyl)nicotinamide.
A-10. 2-Chloro-6-methyl-5-(4-pyridinyl)nicotinamide.
A-11. 2-Chloro-6-ethyl-5-(4-pyridinyl)nicotinamide.
A-12. 2-Chloro-6-methyl-5-(3-pyridinyl)nicotinamide.
A-13. 2-Chloro-6-n-propyl-5-(4-pyridinyl)nicotinamide.
A-14. 2-Chloro-6-isopropyl-5-(4-pyridinyl)nicotinamide.
A-15. 6-n-Butyl-2-chloro-5-(4-pyridinyl)nicotinamide.
A-16. 2-Chloro-6-isobutyl-5-(4-pyridinyl)nicotinamide.

A-17. 2-Chloro-5-(4-pyridinyl)-6-tert.-butylnicotinamide.

A-18. 2-Chloro-6-n-pentyl-5-(4-pyridinyl)nicotinamide.

A-19. 6-Ethyl-2-chloro-5-(2-methyl-4-pyridinyl)-nicotinamide.

A-20. 6-Ethyl-2-chloro-5-(3-pyridinyl)nicotinamide.

B. 2-RR'N-5-PY-6-Q-NICOTINAMIDES

B-1. 2-(2-Hydroxyethylamino)-5-(4-pyridinyl)nicotinamide—A mixture containing 535 g. of 2-chloro-5-(4-pyridinyl)nicotinamide, 309 g. of 2-hydroxyethylamine and 2300 ml. of pyridine was refluxed with stirring for 90 minutes and then allowed to cool. The solvent and excess 2-hydroxyethylamine was distilled off in vacuo. The crystalline residual material was dissolved in hot water and the aqueous solution cooled in ice whereupon an easily filtered tan solid separated. The solid was collected, washed successively with cold water, cold ethanol and ether, and then air-dried to yield 422 g. of 2-(2-hydroxyethylamino)-5-(4-pyridinyl)nicotinamide m.p. >300° C.

Acid-solution salts of 2-(2-hydroxyethylamino)-5-(4-pyridinyl)nicotinamide are conveniently prepared by adding to a mixture of 5 g. of 2-(2-hydroxyethylamino)-5-(4-pyridinyl)nicotinamide in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 2-(2-hydroxyethylamino)-5-(4-pyridinyl)nicotinamide and the appropriate acid, e.g., lactic acid or hydrochloric acid, to prepare respectively the monolactate or monohydrochloride salt in aqueous solution.

B-2. 2-(3-Hydroxypropylamino)-5-(4-pyridinyl)nicotinamide, 20.3 g., m.p. 155°-160° C., was obtained following the procedure described in Example B-1 using 46.7 g. of 2-chloro-5-(4-pyridinyl)nicotinamide, 77.2 ml. of 3-hydroxypropylamine (99%), 300 ml. of pyridine and a reflux period of about 5 hours.

The following procedure also was used to prepare 2-(3-hydroxypropylamino)-5-(4-pyridinyl)nicotinamide: A mixture containing 46.7 g. of 2-chloro-5-(4-pyridinyl)nicotinamide, 77.2 ml. of 3-hydroxypropylamine and 1 liter of absolute ethanol was heated in an autoclave at 100° C. for about 8 hours. The reaction mixture was allowed to cool and was filtered. The filtrate was concentrated in vacuo to remove the ethanol and excess amine to yield an almost quantitative yield of 2-(3-hydroxypropylamino)-5-(4-pyridinyl)nicotinamide, which was used directly in the reaction with sodium hypochlorite in Example C-2 hereinbelow.

B-3. 2-(2-Methoxyethylamino)-5-(4-pyridinyl)nicotinamide—A mixture containing 14.4 g. of 2-chloro-5-(4-pyridinyl)nicotinamide, 35.8 g. of 2-methoxyethylamine and 100 ml. of pyridine was refluxed with stirring for about 5 hours. The pyridine was distilled off in vacuo; the residue was taken up in 100 ml. of water, and, the aqueous solution was chilled to yield a precipitate which was collected and air-dried to yield 3.48 g. of 2-(2-methoxyethylamino)-5-(4-pyridinyl)nicotinamide as its monohydrochloride, m.p. 245°-247° C. Additional product was obtained by concentrating the filtrate in vacuo, taking up the oily material in 200 ml. of isopropyl alcohol and treating the resulting solution with 0.047 M hydrogen chloride in ethanol to precipitate the product. The precipitate was collected and dried at about 125° C. in vacuo for about 16 hours to yield another 8.8 g. of 2-(2-methoxyethylamino)-5-(4-pyridinyl)nicotinamide monohydrochloride, m.p. 244°-247° C.

B-4. 2-Methylamino-5-(4-pyridinyl)nicotinamide—A mixture containing 46.7 g. of 2-chloro-5-(4-pyridinyl)nicotinamide, 92 ml. of 40% aqueous methylamine and 1 liter of 180 proof ethanol was heated in an autoclave at 100° C. for about 8 hours. To the reaction mixture was added excess ammonium hydroxide and the resulting mixture was concentrated in vacuo to yield a solid. The solid was suspended in about 300 ml. of water, the mixture chilled, and the solid collected and dried at 90° C. in vacuo for about 16 hours to yield 29.5 g. of 2-methylamino-5-(4-pyridinyl)nicotinamide, m.p. 250.5°-255° C. A 12.0 g. portion of the product was recrystallized from methanol (400 ml.) -water and dried at 90° C. in a vacuum oven for about 96 hours to yield 10.25 g. of 2-methylamino-5-(4-pyridinyl)nicotinamide, m.p. 258°-261° C.

Acid-addition salts of 2-methylamino-5-(4-pyridinyl)nicotinamide are conveniently prepared by adding to a mixture of 5 g. of 2-methylamino-5-(4-pyridinyl)nicotinamide in about 100 ml. of aqueous methanol the appropriate acid, e.g., methanesulfonic acid, concentrated sulfuric acid, concentrated phosphoric acid, to a pH of about 2-3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 2-methylamino-5-(4-pyridinyl)nicotinamide and the appropriate acid, e.g., lactic acid or hydrochloric acid, to prepare respectively the monolactate or monohydrochloride salt in aqueous solution.

B-5. 2-(2-Dimethylaminoethylamino)-5-(4-pyridinyl)nicotinamide—A mixture containing 25.2 g. of 2-chloro-5-(4-pyridinyl)nicotinamide, 26 g. of 2-dimethylaminoethylamine and 200 ml. of pyridine was refluxed with stirring for about 4 hours and the pyridine was distilled off in vacuo. The solid residue was suspended in isopropyl alcohol and the mixture was made strongly alkaline with concentrated ammonium hydroxide. The resulting mixture was boiled, filtered and the filtrate concentrated to a volume of less than 200 ml. The mixture was cooled and the product collected, dried at 90° C. in a vacuum oven for about 16 hours to yield 9.96 g. of 2-(2-dimethylaminoethylamino)-5-(4-pyridinyl)nicotinamide, m.p. 259°-260° C. with decomposition. An additional 4.35 g. of the product was obtained from the filtrate.

B-6. 2-(2-Hydroxypropylamino)-5-(4-pyridinyl)nicotinamide—A mixture containing 46.7 g. of 2-chloro-5-(4-pyridinyl)nicotinamide, 34 g. of 2-hydroxypropylamine and 350 ml. of pyridine was refluxed with stirring for about 18 hours. The pyridine was distilled off in vacuo and the residue was taken up in isopropyl alcohol. To the alcohol solution was added excess ammonium hydroxide solution and the mixture was concentrated in vacuo. The remaining material was stripped further of volatile material (2-hydroxypropylamine) by heating it in vacuo (by using a water pump) in a oil bath at 170° C. The residue was boiled with 600 ml. of isopropyl alcohol and the solution allowed to cool.

The separated product was collected and dried in a vacuum desiccator over 60 hours to yield 13.6 g. of gummy solid material. The filtrate was treated with excess hydrogen chloride in ethanol to yield more product which was collected, dried, recrystallized from isopropyl alcohol-methanol-ether and dried in vacuo at 90° C. for about 16 hours to yield 12.31 g. of 2-(2-hydroxypropylamino)-5-(4-pyridinyl)nicotinamide as its monohydrochloride, m.p. 222° C. with decomposition. From the filtrate were obtained additional fractions of 8.15 g., 4.23 g. and 2.32 g., m.p. 210° C., 210° C. and 200° C. respectively with decomposition. Still more product was obtained by treating the 13.62 g. of a gummy solid with 300 ml. of methanol; filtering the mixture and treating the filtrate with excess hydrogen chloride in ethanol; diluting the filtrate with ether; collecting the precipitate, drying it and recrystallizing it from methanol-ether to yield another 3.79 g. of 2-(2-hydroxypropylamino)-5-(4-pyridinyl)nicotinamide as its monohydrochloride salt, m.p. 204° C. The various fractions of the product were combined and utilized in Example C-4 hereinbelow without further purification.

B-7. 2-(4-Hydroxybutylamino)-5-(4-pyridinyl)nicotinamide—A mixture containing 46.7 g. of 2-chloro-5-(4-pyridinyl)nicotinamide, 40.6 g. of 4-hydroxybutylamine and 300 ml. of pyridine was refluxed with stirring for 8 hours and the pyridine was then distilled off in vacuo leaving a gummy solid. The solid was suspended in 200 ml. of water and the mixture made alkaline with 15 ml. of concentrated ammonium hydroxide. The resulting mixture was chilled and the resulting precipitate was collected, dried in a vacuum oven at 90° C. for 16 hours to yield 38.89 g. of 2-(4-hydroxybutylamino)-5-(4-pyridinyl)nicotinamide, m.p. 208°-217° C. The product was heated with about 200 ml. of water (major portion remained insoluble) and the insoluble material was collected and dried to yield 28.95 g. of 2-(4-hydroxybutylamino)-5-(4-pyridinyl)nicotinamide, m.p. 221.5°-223.5° C.

Following the procedure of Example B-1, B-4 or B-5 but using in place of 2-chloro-5-(4-pyridinyl)nicotinamide acid and 2-hydroxyethylamine, methylamine or 2-dimethylaminoethylamine molar equivalent quantities of the appropriate 2-halo-5-PY-6-Q-nicotinamide and amine of the formula RNH$_2$, it is contemplated that the corresponding 2-RNH-5-PY-6-Q-nicotinamide of Examples B-8 through B-27 can be obtained.

B-8. 2-n-Propylamino-5-(3-pyridinyl)nicotinamide.
B-9. 2-Isopropylamino-5-(2-methyl-3-pyridinyl)nicotinamide.
B-10. 2-n-Butylamino-5-(5-methyl-3-pyridinyl)nicotinamide.
B-11. 2-Methylamino-5-(3-ethyl-4-pyridinyl)nicotinamide.
B-12. 2-n-Hexylamino-5-(2-methyl-4-pyridinyl)nicotinamide.
B-13. 2-Methylamino-5-(2,6-dimethyl-4-pyridinyl)nicotinamide.
B-14. 2-Ethylamino-5-(4-pyridinyl)nicotinamide.
B-15. 2-Methylamino-6-methyl-5-(4-pyridinyl)nicotinamide.
B-16. 2-(2-Methoxyethylamino)-6-ethyl-5-(4-pyridinyl)nicotinamide.
B-17. 2-Methylamino-6-methyl-5-(3-pyridinyl)nicotinamide.
B-18. 2-Methylamino-6-n-propyl-5-(4-pyridinyl)nicotinamide.
B-19. 2-Methylamino-6-isopropyl-5-(4-pyridinyl)nicotinamide.
B-20. 6-n-Butyl-2-methylamino-5-(4-pyridinyl)nicotinamide.
B-21. 2-(2-Hydroxyethylamino)-6-isobutyl-5-(4-pyridinyl)nicotinamide.
B-22. 2-Methylamino-5-(4-pyridinyl)-6-tert.-butyl-nicotamide.
B-23. 2-(3-Methoxypropylamino)-6-n-pentyl-5-(4-pyridinyl)nicotinamide.
B-24. 6-Ethyl-2-(2-ethoxyethylamino)-5-(2-methyl-4-pyridinyl)nicotinamide.
B-25. 6-Ethyl-2-methylamino-5-(3-pyridinyl)nicotinamide.
B-26. 2-(3-Dimethylaminopropylamino)-5-(4-pyridinyl)nicotinamide.
B-27. 2-[2-(4-Morpholinyl)ethylamino]-5-(4-pyridinyl)nicotinamide.

Following the procedure of Example B-4 but using in place of 40% aqueous methylamine a molar equivalent quantity of 40% aqueous dimethylamine, it is contemplated that the corresponding 2-dimethylamino compound, Example B-28, can be obtained.

B-28. 2-Dimethylamino-5-(4-pyridinyl)nicotinamide.

C.
1,3-DIHYDRO-3-R-6-PY-5-Q-2H-IMIDAZO[4,5-b]PYRIDIN-3-ONES

C-1. 1,3-Dihydro-3-(2-hydroxyethyl)-6-(4-pyridinyl)-2H-imidazo[4,5-b]pyridin-2-one—To a solution containing 288 g. of sodium hydroxide in 6 liters of water was added 623 g. of 2-(2-hydroxyethylamino)-5-(4-pyridinyl)nicotinamide followed by 1200 ml. of 5% aqueous sodium hypochlorite solution. To the reaction mixture was then added slowly with stirring over a period of about 20 minutes 1400 ml. of 10% aqueous sodium hypochlorite solution keeping the reaction mixture between about 20°-30° C. The reaction mixture was then stirred with cooling, keeping the temperature about 25° C., for about 1 hour. The reaction mixture was then heated on a steam bath for 1 hour and then cooled. The pH of the reaction mixture, while cooling, was adjusted to about 6 by addition of acetic acid. Cooling was continued until the reaction mixture was about 10° C. The separated product was collected, washed with cold water and dried to yield 491 g. of a tan solid. This material was combined with another 19.5 g. portion of the product obtained in the same manner and the combined material was recrystallized from dimethylformamide, washed successively with ethanol ane ether, and then dried to yield 416 g. of 1,3-dihydro-3-(2-hydroxyethyl)-6-(4-pyridinyl)-2H-imidazo[4,5-b]pyridin-2-one, m.p. 274°-277° C.

C-2. 1,3-Dihydro-3-(3-hydroxypropyl)-6-(4-pyridinyl)-2H-imidazo[4,5-b]pyridin-2-one, 11.33 g., m.p. 235°-238° C., was obtained following the procedure described in Example C-1 using 20.3 g. of 2-(3-hydroxypropylamino)-5-(4-pyridinyl)nicotinamide, 325 ml. of water, 15.25 g. of sodium hydroxide, 176 ml. of 0.7 M aqueous sodium hypochlorite and a reaction period of about 3 hours at room temperature.

C-3. 1,3-Dihydro-3-(2-methoxyethyl)-6-(4-pyridinyl)-2H-imidazo[4,5-b]pyridin-2-one, 9.54 g., m.p. 203°-206° C., was prepared following the procedure described in Example C-1 using 14.9 g. of 2-(2-methoxyethylamino)-5-(4-pyridinyl)nicotinamide, 175 ml. of water, 6.56 g. of sodium hydroxide, 128 ml. of 0.7 M aqueous sodium hypochlorite, a reaction period of about 5 hours at room temperature and three recrystallizations, two from isopropyl alcohol and one from acetonitrile.

C-4. 1,3-Dihydro-3-(2-hydroxypropyl)-6-(4-pyridinyl)-2H-imidazo[4,5-b]pyridin-2-one as its monohydrochloride hemihydrate, 15.8 g., m.p. 300°–305° C., was prepared following the procedure described above in Example C-1 using 22.65 g. of 2-(2-hydroxypropylamino)-5-(4-pyridinyl)nicotinamide, 350 ml. of water, 8.8 g. of sodium hydroxide and 230.5 ml. of 0.7 M aqueous sodium hypochlorite solution, two recrystallizations from isopropyl alcohol and then conversion of 17.7 g. of the compound in free base form to its hydrochloride hemihydrate salt by treating a solution of it in methanol (600 ml.) with excess hydrogen chloride in ethanol and drying the product in a vacuum oven at 90° C.

C-5. 1,3-Dihydro-3-(4-hydroxybutyl)-6-(4-pyridinyl)-2H-imidazo[4,5-b]pyridin-2-one, 14.5 g., m.p. 222°–223° C., was prepared following the procedure described in Example C-1 using 17.2 g. of 2-(4-hydroxybutylamino)-5-(4-pyridinyl)nicotinamide, 350 ml. of water, 7.20 g. of sodium hydroxide, 188.4 ml. of 0.7 M aqueous sodium hypochloride and a reaction period of about 15 hours at room temperature.

C-6. 3-(2-Dimethylaminoethylamino)-1,3-dihydro-6-(4-pyridinyl)-2H-imidazo[4,5-b]pyridin-2-one, 4.96 g., m.p. 192°–194° C., was prepared following the procedure described in Example C-1 using 27.2 g. of 2-(2-dimethylaminoethylamino)-5-(4-pyridinyl)nicotinamide, 550 ml. of water, 11.42 g. of sodium hydroxide, 224 ml. of 0.7 M aqueous sodium hypochloride solution and several recrystallizations from acetonitrile. The product as its bis(methanesulfonate) was prepared as follows: to a 11.8 g. portion of 3-(2-dimethylaminoethyl)-1,3-dihydro-6-(4-pyridinyl)-2H-imidazo[4,5-b]pyridin-2-one dissolved in 300 ml. of dimethylformamide was treated with 46 ml. of 2 M methanesulfonic acid in ethanol whereupon there separated a yellow-tan precipitate. The suspension was stirred for about an hour and diluted with 600 ml. of ether. The solid was collected by filtration and dried in vacuo at 90° C. for about 16 hours to yield 19.5 g. of 3-(2-dimethylaminoethylamino)-1,3-dihydro-6-(4-pyridinyl)-2H-imidazo[4,5-b]pyridin-2-one bis(methanesulfonate), m.p. 220.5°–222° C.

Following the procedure described in Example C-1 but using in place of 2-(2-hydroxyethylamino)-5-(4-pyridinyl)nicotinamide a molar equivalent quantity of the appropriate 2-RNH-5-PY-6-Q-nicotinamide, it is contemplated that the 1,3-dihydro-3-R-6-PY-5-Q-2H-imidazo[4,5-b]pyridin-2-ones of Example C-7 thru C-25 can be obtained.

C-7. 1,3-Dihydro-3-methyl-6-(4-pyridinyl)-2H-imidazo[4,5-b]pyridin-2-one, m.p., >300° C., using 2-methylamino-5-(4-pyridinyl)nicotinamide.

C-8. 3-Ethyl-1,3-dihydro-6-(4-pyridinyl)-2H-imidazo[4,5-b]pyridin-2-one, m.p. 244°–246° C., using 2-ethylamino-5-(4-pyridinyl)nicotinamide.

C-9. 1,3-Dihydro-3-(3-dimethylaminopropyl)-6-(4-pyridinyl)-2H-imidazo[4,5-b]pyridin-2-one, m.p. 188°–191° C., using 2-(3-dimethylaminopropyl)-5-(4-pyridinyl)-nicotinamide.

C-10. 1,3-Dihydro-3-[2-(4-morpholinyl)ethyl]-6-(4-pyridinyl)-2H-imidazo[4,5-b]pyridin-2-one, m.p. 186°–190° C., using 2-[2-(4-morpholinyl)ethylamino]-5-(4-pyridinyl)nicotinamide.

C-11. 1,3-Dihydro-3-n-propyl-6-(3-pyridinyl)-2H-imidazo[4,5-b]pyridin-2-one using 2-n-propylamino-5-(3-pyridinyl)nicotinamide.

C-12. 1,3-Dihydro-3-isopropyl-6-(2-methyl-5-pyridinyl)-2H-imidazo[4,5-b]pyridin-2-one using 2-isopropylamino-5-(2-methyl-5-pyridinyl)nicotinamide.

C-13. 3-n-Butyl-1,3-dihydro-6-(5-methyl-3-pyridinyl)-2H-imidazo[4,5-b]pyridin-2-one using 2-n-butylamino-5-(5-methyl-3-pyridinyl)nicotinamide.

C-14. 1,3Dihydro-3-n-hexyl-6-(2-methyl-4-pyridinyl)-2H-imidazo[4,5-b]pyridin-2-one using 2-n-hexylamino-5-(2-methyl-4-pyridinyl)nicotinamide.

C-15. 1,3-Dihydro-3-methyl-6-(2,6-dimethyl-4-pyridinyl)-2H-imidazo[4,5-b]pyridin-2-one using 2-methylamino-5-(2,6-dimethyl-4-pyridinyl)nicotinamide.

C-16. 1,3-Dihydro-3-methyl-5-n-propyl-6-(4-pyridinyl)-2H-imidazo[4,5-b]pyridin-2-one using 2-methylamino-6-n-propyl-5-(4-pyridinyl)nicotinamide.

C-17. 1,3-Dihydro-5-isopropyl-3-methyl-6-(4-pyridinyl)-2H-imidazo[4,5-b]pyridin-2-one using 2-methylamino-6-isopropyl-5-(4-pyridinyl)nicotinamide.

C-18. 1,3-Dihydro-5-n-butyl-3-methyl-6-(4-pyridinyl)-2H-imidazo[4,5-b]pyridin-2-one using 6-n-butyl-2-methylamino-5-(4-pyridinyl)nicotinamide.

C-19. 1,3-Dihydro-3-(2-hydroxyethyl)-5-isobutyl-6-(4-pyridinyl)-2H-imidazo[4,5-b]pyridin-2-one using 2-(2-hydroxyethylamino)-6-isobutyl-5-(4-pyridinyl)-nicotinamide.

C-20. 1,3-Dihydro-3-methyl-6-(4-pyridinyl)-5-tert.-butyl-2H-imidazo[4,5-b]pyridin-2-one using 2-methylamino-5-(4-pyridinyl)-6-tert.-butylnicotinamide.

C-21. 1,3-Dihydro-3-(3-methoxypropyl)-5-n-pentyl-6-(4-pyridinyl)-2H-imidazo[4,5-b]pyridin-2-one using 2-(3-methoxypropylamino)-6-n-pentyl-5-(4-pyridinyl)-nicotinamide.

C-22. 1,3-Dihydro-3-(2-ethoxyethyl)-5-ethyl-6-(2-methyl-4-pyridinyl)-2H-imidazo[4,5-b]pyridin-2-one using 6-ethyl-2-(2-ethoxyethylamino)-5-(2-methyl-4-pyridinyl)nicotinamide.

C-23. 5-Ethyl-1,3-dihydro-3-methyl-6-(3-pyridinyl)-2H-imidazo[4,5-b]pyridin-2-one using 6-ethyl-2-methylamino-5-(3-pyridinyl)nicotinamide.

C-24. 1,3-Dihydro-5-ethyl-3-(2-methoxyethyl)-6-(4-pyridinyl)-2H-imidazo[4,5-b]pyridin-2-one using 2-(2-methoxyethylamino)-6-ethyl-5-(4-pyridinyl)nicotinamide.

C-25. 1,3-Dihydro-3,5-dimethyl-6-(3-pyridinyl)-2H-imidazo[4,5-b]pyridin-2-one using 2-methylamino)-6-methyl-5-(3-pyridinyl)nicotinamide.

The usefulness of the compounds of formula II or salts thereof as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in the U.S. Pat. No. 4,072,746, issued Feb. 7, 1980.

When tested by the isolated guinea pig atria and papillary muscle procedure, the compounds of formula II or pharmaceutically-acceptable acid-addition salts thereof at doses of 10, 30, 100 μg./ml., were found to cause significant increases, that is, greater than 30% in papillary muscle force and significant increases, that is, greater than 30%, in right atrial force, while causing a lower percentage increase (about one-third or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at said dose levels by this procedure, the following preferred compound of Example B-4 was found to cause respective increases in papillary muscle force and right atrial force of 62% and 33% at 10 μg/ml., 89% and 62% at 30 μg/ml and 122% and 118% at 100 μg/ml.

The present invention includes within its scope a cardiotonic composition for increasing cardiac contractility, said composition comprising a pharmaceutically acceptable carrier and, as the active component thereof, the cardiotonic compound of formula II or pharmaceutically acceptable acid-addition salt thereof. The invention also includes within its scope the method for increasing cardiac contractility in a patient requiring such treatment which comprises administering to such patient an effective amount of a cardiotonic compound of formula II or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also includes capsules of absorbable material, such as gelatin, containing said active component with or without the addition of diluents or excipients.

Preparations according to the invention for parenteral administration include sterile aqueous, aqueous-organic, and organic solutions, suspension and emulsions. Examples or organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other injectable medium immediately before use.

The percentages of active component in the said compositions and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 2-RR'N-5-PY-6-Q-nicotinamide having the formula

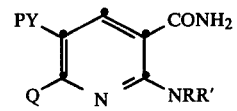

where Q is hydrogen or lower-alkyl, R is lower-alkyl, lower-hydroxyalkyl, lower-alkoxyalkyl or Y-NB where Y is lower-alkylene having at least two carbon atoms between its connecting linkages, R' is hydrogen or methyl and PY is 4- or 3-pyridinyl or 4- or 3-pyridinyl having one or two lower-alkyl substituents, or pharmaceutically acceptable acid-addition salt thereof.

2. A compound according to claim 1 where PY is 4-pyridinyl or 3-pyridinyl, R is methyl, ethyl, 2-hydroxyethyl or 2-hydroxypropyl, R' is hydrogen or methyl and Q is hydrogen, methyl or ethyl.

3. 2-(2-Hydroxyethylamino)-5-(4-pyridinyl)nicotinamide or pharmaceutically acceptable acid-addition salt thereof.

4. 2-(2-Hydroxypropylamino)-5-(4-pyridinyl)-nicotinamide or pharmaceutically acceptable acid-addition salt thereof.

5. 2-Methylamino-5-(4-pyridinyl)nicotinamide or pharmaceutically acceptable acid-addition salt thereof.

6. A cardiotonic composition for increasing cardiac contractility, said composition comprising a pharmaceutically acceptable inert carrier and, as the active component thereof, a cardiotonically effective amount of 2-RR'N-5-PY-6-Q-nicotinamide or pharmaceutically acceptable acid-addition salt thereof, where Q is hydrogen or lower-alkyl, R is lower-alkyl, lower-hydroxyalkyl, lower-alkoxyalkyl or Y-NB where Y is lower-alkylene having at least two carbon atoms between its connecting linkages, R' is hydrogen or methyl and PY is 4- or 3-pyridinyl or 4- or 3-pyridinyl having one or two lower-alkyl substituents.

7. A composition according to claim 6, where PY is 4-pyridinyl or 3-pyridinyl, R is methyl, ethyl, 2-hydroxyethyl or 2-hydroxypropyl, R' is hydrogen or methyl and Q is hydrogen, methyl or ethyl.

8. A composition according to claim 6 where the active component is 2-methylamino-5-(4-pyridinyl)-nicotinamide or pharmaceutically-acceptable acid-addition thereof.

9. The method for increasing cardiac contractility in a patient requiring such treatment which comprises administering orally or parenterally in a solid or liquid dosage form to such patient said cardiotonic composition of claim 6.

10. The method for increasing cardiac contractility in a patient requiring such treatment which comprises administering orally or parenterally in a solid or liquid dosage form to such patient said cardiotonic composition of claim 7.

11. The method for increasing cardiac contractility in a patient requiring such treatment which comprises administering orally or parenterally in a solid or liquid dosage form to such patient said cardiotonic composition of claim 8.

* * * * *